United States Patent [19]

Prager

[11] Patent Number: 4,954,624
[45] Date of Patent: Sep. 4, 1990

[54] PROCESS FOR THE PRODUCTION OF CEPHALOSPORIN DERIVATIVES

[75] Inventor: Bernhard C. Prager, Wörgl, Austria

[73] Assignee: Sandoz Ltd., Basel, Switzerland

[21] Appl. No.: 385,591

[22] Filed: Jun. 29, 1989

Related U.S. Application Data

[63] Continuation of Ser. No. 213,570, Jun. 7, 1988, abandoned.

[51] Int. Cl.$^5$ ............... C07D 501/38; A61K 31/545
[52] U.S. Cl. ..................................... 540/225; 514/206
[58] Field of Search ......................... 540/225; 514/206

[56] References Cited

U.S. PATENT DOCUMENTS

| | | | |
|---|---|---|---|
| 4,258,041 | 3/1981 | O'Callaghan et al. | 540/225 |
| 4,659,813 | 4/1987 | Bruning et al. | 540/225 |
| 4,769,450 | 9/1988 | Stone et al. | 540/225 |

FOREIGN PATENT DOCUMENTS

| | | |
|---|---|---|
| 0157538 | 10/1985 | European Pat. Off. . |
| 0179546 | 4/1986 | European Pat. Off. . |
| 0187450 | 7/1986 | European Pat. Off. . |
| 2466467 | 4/1987 | France . |

Primary Examiner—Nicholas S. Rizzo
Attorney, Agent, or Firm—Gerald D. Sharkin; Robert S. Honor; Thomas O. McGovern

[57] ABSTRACT

New process for the production of the pentahydrate of ceftazidime of formula

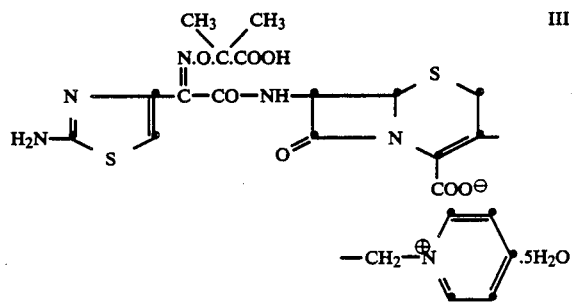

characterized in that the ester group of the compound of formula

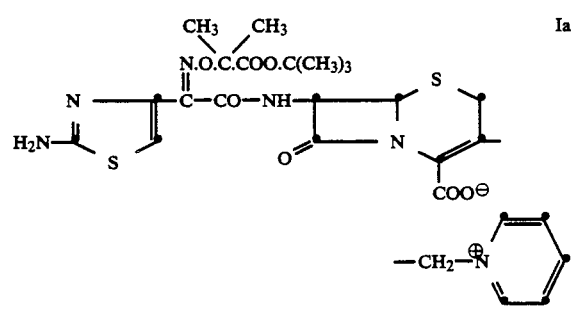

or an acid addition salt thereof, is cleaved by the sole use of aqueous hydrochloric acid, and the resulting ceftazidime is either crystallized directly from the reaction mixture as the pentahydrate by adding a base, or first of all the dihydrochloride of the ceftazidime is isolated by adding acetone and/or ethanol or another anti-solvent which is miscible with water, and this is converted into the pentahydrate by known methods.

15 Claims, No Drawings

PROCESS FOR THE PRODUCTION OF CEPHALOSPORIN DERIVATIVES

This is a continuation of application Ser. No. 07/213,570, filed June 7, 1988, now abandoned.

The invention relates to an improved, simplified and new process for the production of the antibiotic ceftazidime pentahydrate.

Ceftazidime is a valuable antibiotic. The production thereof is described, among other things, in GB-PS No. 2025 398. Ceftazidime may be obtained in various forms, as the dihydrochloride, dihydrobromide or as the pentahydrate. The pentahydrate is the preferred form and is described for example in GB-PS 2063 871. The known processes, which lead to this preferred form of the pentahydrate, follow the course drafted in the following formula scheme:

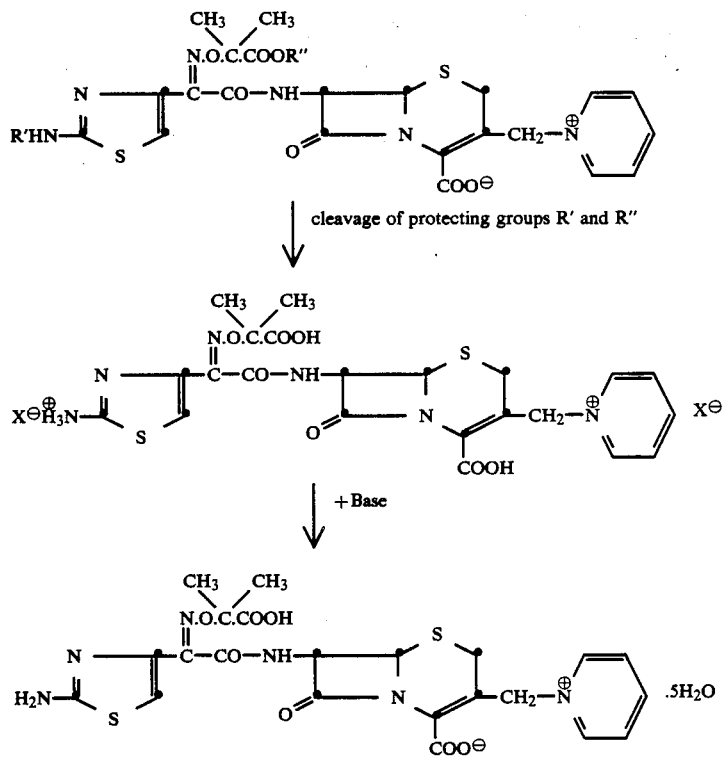

In the processes for the production of ceftazidime pentahydrate (formula III) which are known from literature, first of all the compounds of formula II, which represent ceftazidime as the dihydrohalide, are produced and isolated from compounds of formula I, which represents the simple (R'=hydrogen) or double-protected (R'=protecting group) ceftazidime, or purification of the ceftazidime from the cleavage products is attained by extraction processes, before the ceftazidime can be isolated as the pentahydrate. This intermediate isolation of the dihalide or the purification of the solution containing the ceftazidime after cleavage of the protecting groups is necessary, since the cleavage products arising when the protecting groups are split off prevent crystallisation of the pure pentahydrate, or at least make it extremely difficult. In addition, because of the use of considerable amounts of organic acids to split off the protecting groups (usually formic acid), when the ceftazidime is directly isolated as the pentahydrate without intermediate isolation of the ceftazidime as the dihydrohalide, a considerable amount of salt is produced upon precipitation of the pentahydrate, which takes place at a pH value of about 3.6 to 4, which again to a great extent prevents crystallisation of the ceftazidime as the pentahydrate.

In accordance with the invention, it has now surprisingly been found that it is possible to crystallise the pentahydrate of the ceftazidime directly from the compound of formula I, wherein R'=H and R''=t-butyl, without having to go through the isolated intermediate stage of a dihalide. The process according to the invention is characterised in that only hydrochloric acid is used during the cleavage of the protecting group R''=t-butyl.

Whilst in the known processes, as well as using hydrochloric acid, further (organic) acids which usually also serve as solvents are used, such as formic acid, dichloroacetic acid, trifluoroacetic acid or trichloroacetic acid, the process according to the invention is restricted to the sole use of hydrochloric acid. Due to the omission of the other (usually organic) acids, a considerable advantage is obtained, which is that when there is direct processing to the pentahydrate, which is isolated at about pH 3.6 to 4, only the hydrochloric acid employed must be neutralised, while in the case of the additional use (or even sole use) of an organic acid in a large excess, as is normal with conventional processes, a vast amount of salt is produced in the direct neutralisation process, which makes crystallisation of the pentahydrate of ceftazidime very difficult.

A further advantage of the process according to the invention is the high concentration at which the process is carried out— whereby large quantities of product can be produced in little time and with a small reactor volume. A further advantage of the process according to the invention is that, apart from hydrochloric acid (and a base for neutralisation), no chemicals or solvents are required, which represents a considerable financial and ecological advantage.

However, apart from all these advantages of the process according to the invention, there is also the possibility of isolating the intermediate stage of the dihydrochloride of ceftazidime (formula II; X=chloride), whereby this also gives the advantages regarding ecology and more simple reclaimability of the solvents. In the process according to the invention, when isolating the compound of formula II, a further advantage becomes clear, since as a result of the sole use of hydrochloric acid for ester cleavage, the compound of formula II can be obtained particularly easily and in highly pure form. In contrast to known processes—in which the reaction mixture is usually saturated with vast amounts of acetone—the process according to the invention allows simple and slow crystallisation of the dihydrochloride of ceftazidime to take place by simply adding solvents such as acetone and/or ethanol to the reaction mixture, whereupon the dihydrochloride of ceftazidime is obtained in highly pure form in crystals which can be readily isolated. The dihydrochloride isolated in this way is notable for its very high purity (HPLC≧93%), which brings considerable advantages in the transformation into the pentahydrate of ceftazidime (increased crystallisation yields).

When isolating the dihydrochloride, the mother liquor can be regenerated or resp. removed in a simple way, since it does not contain any solvents apart from the acetone and hydrochloric acid and small quantities of iso-butene. For this, it is sufficient to neutralise the mother liquor using (optionally solid) alkali lye (to avoid corrosion in distillation) and to distill off or resp. rectify the acetone. The acetone obtained can then be used again to precipitate the compound of formula II.

The process according to the invention, which instead of the otherwise usual organic acids or resp. mixtures of organic acids with a hydro-halic acid, is restricted to the sole use of aqueous hydrochloric acid for cleavage of compounds of formula I, thus allows both the production of the compound of formula II (X=chloride) which is regarded as an intermediate stage, and the direct recovery of the pentahydrate of ceftazidime (fomula III) in highly pure form (≧97% on an anhydrous basis) and in an excellent yield (70% and higher) to be effected in a simple manner.

In the process according to the invention, the t-butylester of ceftazidime may be used in any crystal form or also as an acid addition salt.

The following examples illustrate the invention more fully, but in no way limit it. All temperatures are given in degrees centigrade. The water evaluations were made by the Karl-Fischer method.

EXAMPLE 1

Ceftazidime Pentahydrate 65 g of ceftazidime-t-butylester (crystalline in β-form) are added at 0° to 5° to 80 ml of conc. HCl (11 normal), whereby a light yellow solution is produced. This is stirred for another 1 hour at 5°, until ester cleavage is complete (thin-layer chromatography or HPLC). Then, 80 ml of ice water are added to the solution, and the pH value is adjusted to 4.1 with 5 N NaOH at a max. of +5°. The solution is left to stand for 1 hour at 5° to 10°, whereby the product begins to crystallise out. Then, the pH value is adjusted to 3.8 with 3 N HCl, and after a further one hour to pH 3.6, whereby the temperature is always kept at between +5° and +10°. Finally, cooling is effected to 0° to 4° for 5 hours. The precipitated crystals are then filtered off, washed with cold water and acetone, and dried at room temperature. 46.5 g of the title compound are obtained (73% of theory) in the form of a white crystalline powder.

content (HPLC; on H₂O-free basis): 97.0% water content (Karl-Fischer): 14.5%

EXAMPLE 2

Ceftsazidime Pentahydrate 70.2 g of ceftazidime-t-butylester (crystalline in α-form) are added at 0° to 5° to 100 ml of conc. HCl, whereby a light yellow-greenish solution is produced. This is stirred for about 1 hour at 5°. Then, 120 ml of ice water are added, followed by solid sodium bicarbonate, until a pH value of 4.0–4.1 has been attained. The temperature is kept at below +5°. The mixture is then left to stand for 1 to 2 hours at about 10° to 15°, whereby the product begins to crystallise out. Then, the pH value is adjusted to 3.6 with 3N HCl, and the mixture is left to stand for another 5 hours at 0° to 4°. The title compound is then isolated, washed with cold water and acetone, and dried. In this way, 44.3 g (70%) of the title compound are obtained in pure form (HPLC content: 97.3%, H₂O content: 14.6%).

EXAMPLE 3

Ceftazidime Dihydrochloride 130 g of ceftazidime-t-butylester (crystalline in β-form) are added at 10° to 150 ml of conc. HCl, whereby a yellow solution is produced. This is stirred for a further one hour at 10°. Then 300 ml of acetone are added and allowed to crystallise for 30 minutes. The product separates in the form of fine regular crystals. To complete crystallisation, a further 700 ml of acetone are added over the course of 90 minutes, and stirring is effected for one hour. The crystals are subsequently isolated, washed with acetone and vacuum-dried. 120 g (97%) of the title compound are obtained in the form of white drippable crystals with a content of 94% (HPLC).

EXAMPLE 4

Ceftazidime Pentahydrate 60 g of the ceftazidime dihydrochloride obtained as described in Example 3 are dissolved in 300 ml of ice water. The acidic (pH 0.7–0.8) solution is clear-filtered to remove solid particles and the pH is then adjusted to 4.0 with about 160 ml of 3N NaOH at a maximum of 10°. After crystallisation for 2 hours, the pH is adjusted to 3.6 and crystallisation continues for 3 hours at about 5°. The product is then filtered off by suction, washed with cold water and acetone and dried. 50 g (87%) of the title compound are obtained in the form of colourless crystals with a content of ≧97%.

I claim:

1. A process for the preparation of the pentahydrate of ceftazidime of formula III

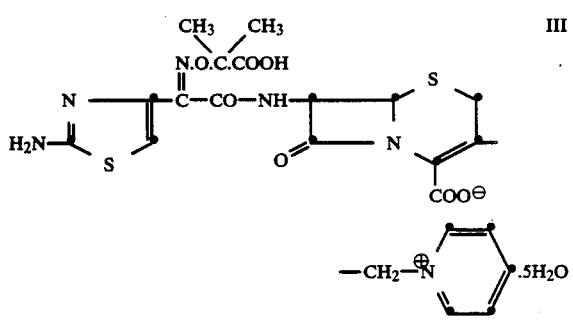

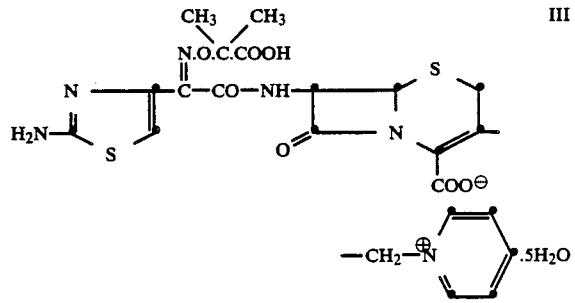

which consist essentially of the steps:
(a) hydrolyzing the ester of formula Ia

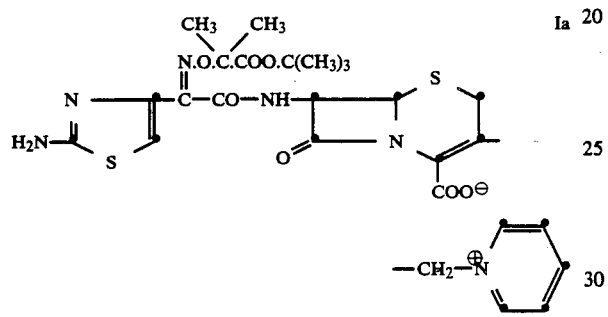

in concentrated hydrochloric acid to form an aqueous solution of the dihydrochloride salt of formula II

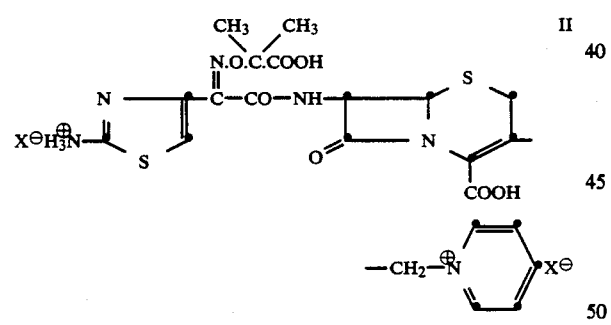

where X is a chloride anion, and
(b) adjusting the pH of the aqueous solution of the dihydrochloride salt of formula II from step a to 3.6 to 4.1 with a base to obtain the pentahydrate of formula (III).

2. A process according to claim 1, in which the pH in step b is adjusted with sodium hydroxide.

3. A process according to claim 1, in which the pH is adjusted with sodium bicarbonate.

4. A process according to claim 1 in which the process is carried out between 0° to 10° C.

5. A process for the preparation of the pentahydrate of cetazidime of formula III which consist essentially of the steps:
(a) hydrolyzing the ester of formula Ia in concentrated aqueous hydrochloric acid to form an aqueous solution of the dihydrochloride salt of formula II

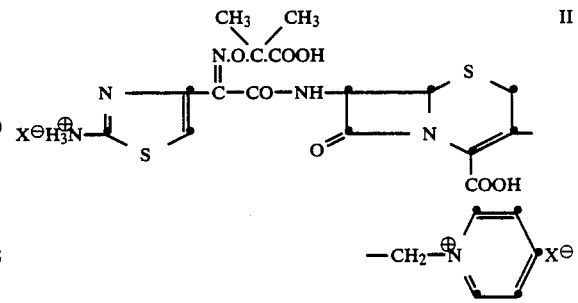

where X is a chloride anion;
(b) crystallizing the dihydrochloride salt out of solution by adding an anti-solvent miscible with water and separating the salt from the aqueous solvent; and
(c) dissolving the dihydrochloride salt in water and adjusting the pH of the solution to 3.6 to 4.1 to obtain the pentahydrate of formula (III).

6. A process according to claim 5 in which the concentration of the concentrated aqueous hydrochloric acid is 20% to 40% by weight.

7. A process according to claim 5, in which the anti-solvent in step b is acetone.

8. A process according to claim 5, in which the anti-solvent in step b is ethanol.

9. A process according to claim 5, in which the pH in step c is adjusted with sodium hydroxide.

10. A process for the production of ceftazidime dihydrochloride of formula II

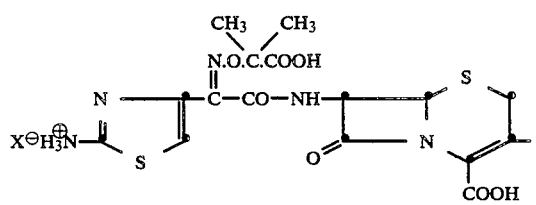

where X is a chloride anion, which consists essentially of the steps:

(a) hydrolyzing an ester of formula Ia

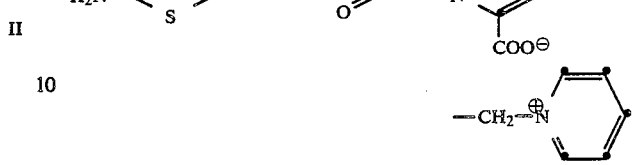

in concentrated aqueous hydrochloric acid to form an aqueous solution of the dihydrochloride salt of formula II, and (b) crystallizing the dihydrochloride salt out of solution by adding an anti-solvent miscible with water and separating the salt from the aqueous solvent.

11. A process according to claim 10, in which the concentration of the concentrated aqueous hydrochloric acid is 20% to 40% by weight.

12. A process according to claim 10, in which the anti-solvent in step b is acetone.

13. A process according to claim 10, in which the anti-solvent in step b is ethanol.

14. Process according to claim 1, characterized in that the concentration of the aqueous hydrochloric acid is 20 to 40% by weight.

15. Process according to claims 1 and 14, characterised in that the ester cleavage is carried out at −15° to +35° C.

* * * * *